United States Patent

Smale

[11] 3,951,951
[45] Apr. 20, 1976

[54] AZETIDINONES

[75] Inventor: Terence Charles Smale, Epsom Downs, England

[73] Assignee: Beecham Group Limited, England

[22] Filed: Oct. 11, 1974

[21] Appl. No.: 514,073

[52] U.S. Cl. .................. 260/239 A; 260/243 C; 260/326 S
[51] Int. Cl.² .............. C07D 205/08; C07D 403/04; C07D 501/02
[58] Field of Search.................... 260/239 A, 326 S

[56] References Cited
OTHER PUBLICATIONS
Nayler et al., Chem. Abs. 78, 111335t (1973).

Primary Examiner—Alton D. Rollins
Assistant Examiner—Mark L. Berch

[57] ABSTRACT

Compounds are provided of the formula (I):

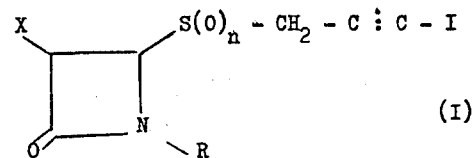

wherein n is 0 or 1, X is a substituted amino group which is convertible to an amino group or salt thereof and R is hydrogen or a group of the formula (II) or (III):

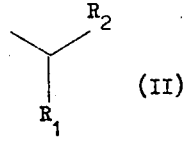 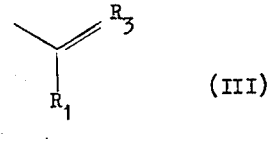

wherein $R_1$ is an ester group convertible to a carboxylic acid group or a salt thereof, $R_2$ is OH or Cl and $R_3$ is $C(CH_3)_2$ or $PR_aR_bR_c$ where $R_a$, $R_b$ and $R_c$ are each a $C_{1-6}$ alkyl, phenyl, toluyl or benzyl group. Such compounds are of value as intermediates in the synthesis of antibacterially active cephalosporin compounds.

5 Claims, No Drawings

AZETIDINONES

The substituted azetidin-2-ones which are of value as intermediates in the synthesis of antibacterially active cephalosporin compounds are of the formula (I):

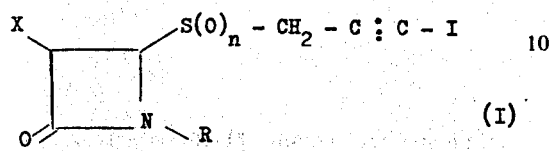

wherein $n$ is 0 or 1, X is a substituted amino group which is convertible to an amino group or salt thereof and R is hydrogen or a group of the formula (II) or (III):

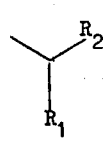 (II)     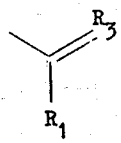 (III)

wherein $R_1$ is an ester group convertible to a carboxylic acid group or a salt thereof, $R_2$ is OH or Cl and $R_3$ is $C(CH_3)_2$ or $PR_aR_bR_c$ where $R_a$, $R_b$ and $R_c$ are each a $C_{1-6}$ alkyl, phenyl, toluyl or benzyl group.

The use of such compounds may be understood by reference to the reaction sequence shown in the following flow diagram and analagous processes:

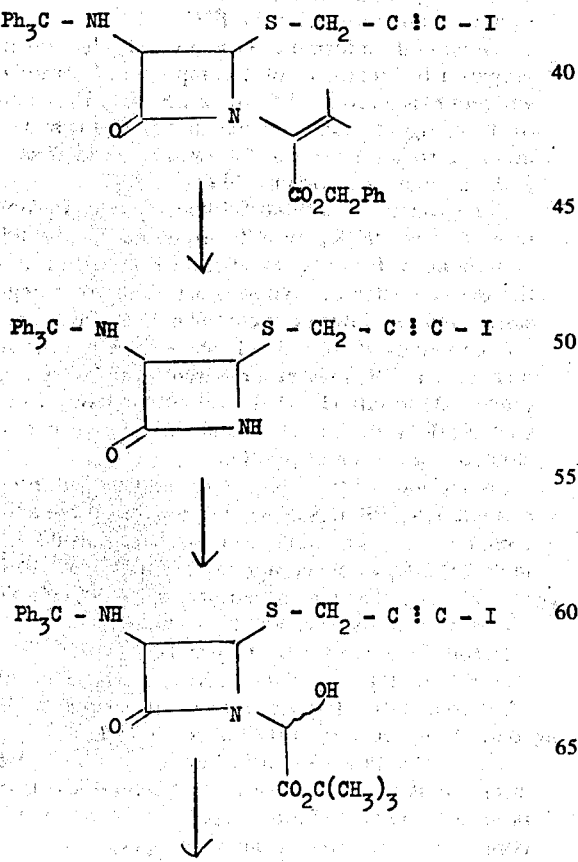

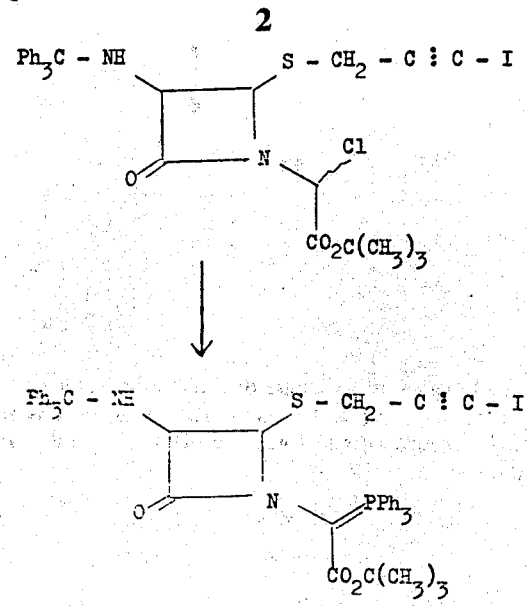

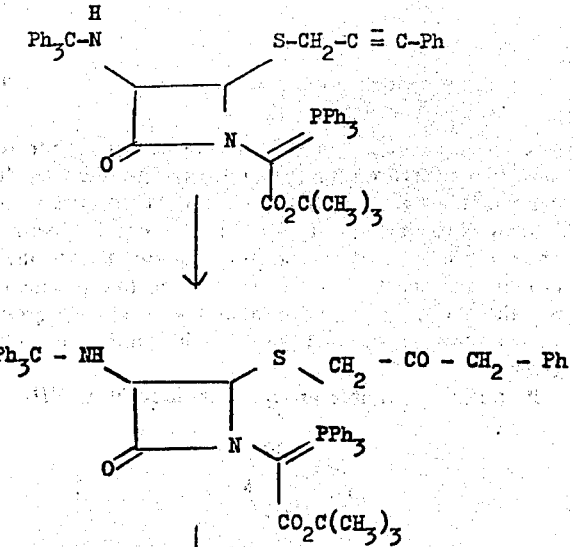

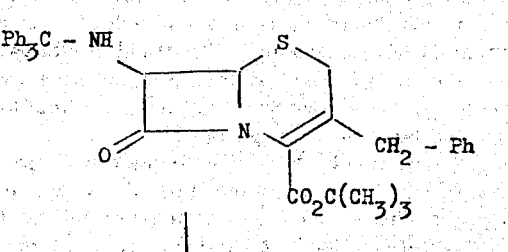

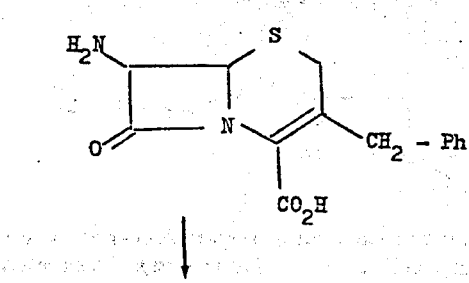

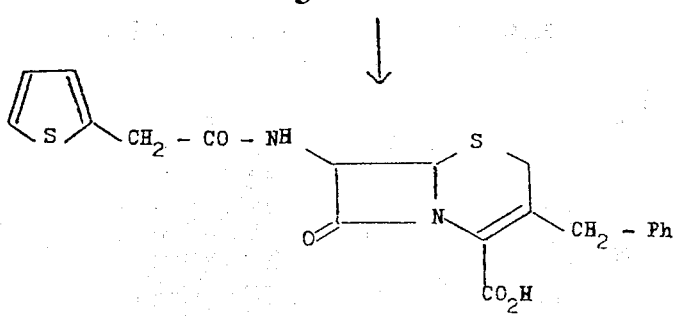

Suitable groups X include the inert substituted amino groups convertible to free or salted amino groups and include groups of the formulae (IV), (V), (VI) and (VII):

$$R_4\text{—NH—} \quad (IV)$$

$$R_5\text{—CO—NH—} \quad (V)$$

$$\begin{array}{c}R_6\text{—CO}\\ \phantom{R_6}\diagdown\\ \phantom{R_6\text{—CO}}N\text{—}\\ \phantom{R_6}\diagup\\ R_7\text{—CO}\end{array} \quad (VI)$$

$$R_8\text{—O—CO—NH—} \quad (VII)$$

wherein $R_4$ is bulky, inert amino-protecting group removable by hydrogenation or hydrolysis such as the triphenylmethyl and chemically equivalent groups; $R_5$ is a non-reactive group such as the phenyl, benzyl, phenoxymethyl and like groups; $R_6$ and $R_7$ are inert groups such as the benzyl, methyl and like groups or together form a phenyl group; and $R_8$ is an inert group such as the tert-butyl, benzyl, trichloroethyl and like groups.

Particularly suitable groups X include $Ph_3C\text{-NH-}$;

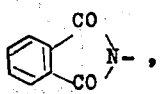

$(CH_3)_3C\text{-O-CO-NH-}$, $Cl_3C\text{-CH}_2\text{-O-CO-NH-}$, $Ph\text{-CH}_2\text{-CO-NH}$, $Ph\text{-O-CH}_2\text{-CO-NH}$ and the like.

Suitable groups $R_1$ include those known in the penicillin and cephalosporin arts to be readily convertible to free or salted carboxyl groups and include benzyloxycarbonyl, t-butoxycarbonyl, 2,2,2-trichloroethoxycarbonyl, diphenylmethoxycarbonyl, p-methoxybenzyloxycarbonyl, p-nitrobenzyloxycarbonyl, p-methoxyphenoxycarbonyl and like groups.

Suitable groups $R_a$, $R_b$ and $R_c$ include inert groups such as methyl, ethyl, propyl, phenyl, benzyl, inert substituted phenyl, inert substituted benzyl and like groups. Preferably, $R_a$, $R_b$ and $R_c$ are each phenyl groups.

Particularly valuable intermediates of formula (I) include those of formula (VII):

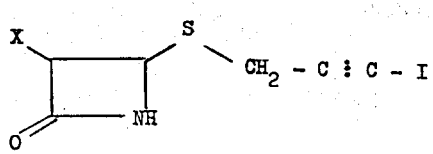

and their corresponding sulphoxides wherein X is as previously defined. In such compounds, X is preferably a triphenylmethylamino, phenylacetamido or phenoxyacetamido group.

Compounds of formula (I) wherein R is a $CR_1 = C(CH_3)_2$ group may be prepared by contacting a source of positive iodine and a compound of the formula:

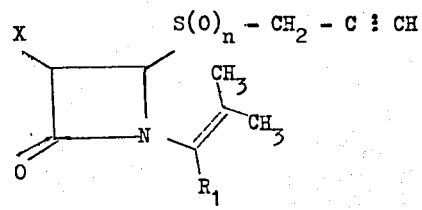

wherein $n$, X and $R_1$ are as defined in relation to formula (I).

Preferably, the source of positive iodine is iodine nitrate which can be prepared in situ by the reaction of silver nitrate and iodine monochloride.

The reaction may be carried out in a variety of inert organic solvents such as chloroform, dichloromethane or the like but preferably, the reaction mixture contains a weak base such as pyridine to act as an acid acceptor. When $INO_3$ is used as the source of positive iodine, the pyridine complexes with the $INO_3$.

Compounds of formula (I) wherein R is hydrogen are prepared by treatment of a compound of formula (I) wherein R is a group of formula $CR_1:C(CH_3)_2$ with an oxidising agent, such as potassium permanganate, osmium tetroxide or ozone followed by mild treatment with aqueous or alcoholic alkali.

Compounds of formula (I) wherein R is a group of formula $CH(OH)R_1$ may be prepared by reacting a compound of formula (I) wherein R is hydrogen with the desired ester of glyoxylic acid and removing the water generated during the course of the reaction.

Compounds of formula (I) wherein R is a group of formula $CHClR_1$ may be prepared by reacting a compound of formula (I) wherein R is a group of formula $CH(OH)R_1$ with thionyl chloride in the presence of an acid acceptor such as pyridine.

Compounds of formula (I) wherein R is a group of formula $CR_1:PR_aR_bR_c$ may be prepared by reacting a compound of formula (I) wherein R is a group of formula $CHClR_1$ with a compound of formula $PR_aR_bR_c$ in the presence of an acid acceptor, wherein $R_a$, $R_b$ and $R_c$ are as defined with respect to formula (I).

Naturally, compounds of formula (I) wherein $n = 1$ may be prepared from the corresponding compounds wherein $n = 0$ by known oxidation procedures such as those described in British Pat. No. 1,280,693.

The compounds of this invention are of value as intermediates in the preparation of cephalosporin compounds by virtue of their capacity to react with aryl copper reagents such as phenyl copper:

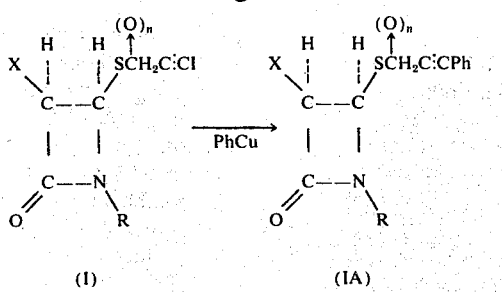

(I)  →PhCu→  (IA)

The following Examples illustrate the present invention.

EXAMPLE 1

1-(1-Benzyloxycarbonyl-2-methyl-1-propenyl)-4-(3-iodopropargylthio)-3-triphenylmethylaminoazetidin-2-one

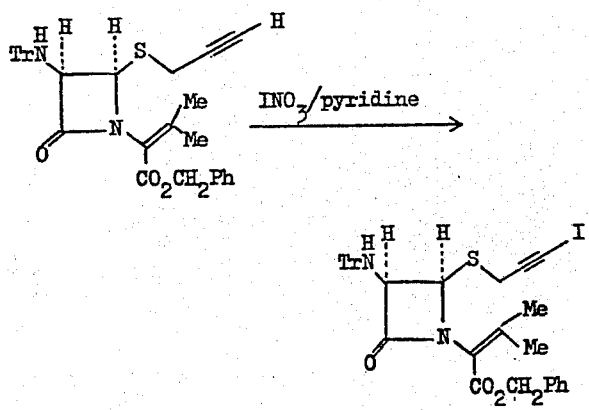

A solution of silver nitrate (12.6 g.) in chloroform (100 ml.) and pyridine (50 ml.) was stirred and cooled in an ice bath. A solution of iodine monochloride (4.2 ml.) in chloroform (50 ml.) was added over a period of 5 mins. The precipitated silver chloride was removed from the iodonium nitrate solution by centrifugation and the precipitate was washed with pyridine (50 ml.). The washings were combined with the bulk solution.

The reagent solution was stirred and treated with a solution of 1-(1-benzyloxycarbonyl-2-methylprop-1-enyl)-4-propargylthio-3-triphenylmethylaminoazetidin-2-one (28.0 g.) in chloroform (50 ml.) and stirred at room temperature for 4 hours. The solvent was distilled from the product under reduced pressure and the residue was partitioned between ethyl acetate and water. The ethyl acetate solution was dried over sodium sulphate and concentrated to a brown syrup which was mainly a single compound by t.l.c. It was purified by column chromatography on silica gel 60 (<230 mesh) eluting with ethyl acetate/60°–80° petroleum ether 3:7. The product was a pale yellow foam (25.9 g., 76%); $\nu_{max}$ (CHCl$_3$) 2980, 1765, 1715 and 1630 cm$^{-1}$; $\tau$ 2.3-2.9 (20H, m, phenyls), 4.71 and 4.96 (2H, ABq J=12Hz, benzyl CH$_2$), 5.15 (1H, d J=5Hz, C4), 5.40 (1H, broad m, C3), 6.95 and 7.30 (2H, ABq J=17Hz, S-CH$_2$), ca. 7.1 (1H, broad, NH), 7.73 (3H, s, =C(−CH$_3$))

and 7.98 (3H, s, =C(−CH$_3$)).

(M$^+$ at m/e 712.1291. C$_{37}$H$_{33}$IN$_2$O$_3$S requires 712.1258).

EXAMPLE 2

4-(3-Iodopropargylthio)-3-triphenylmethylaminoazetidin-2-one

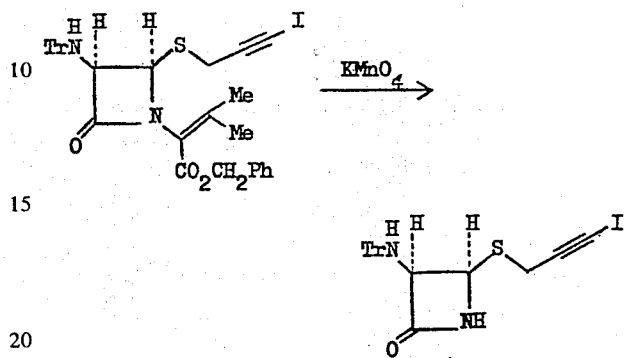

1-(1-Benzyloxycarbonyl-2-methyl-1-propenyl)-4-(3-iodopropargylthio)-3-triphenylmethylaminoazetidin-2-one (25.9 g.) in dimethyl formamide (200 ml.), pyridine (10 ml.) and water (20 ml.) was stirred and cooled in an ice-salt bath. It was treated with powdered potassium permanganate (8.8 g.) over a period of 15 minutes, and then stirred for a further 2 hours. The dark mixture was diluted with ethyl acetate (500 ml.) and sulphur dioxide passed through until it just decolorised. The product was washed with brine and dried over sodium sulphate. The solution was concentrated to a syrup which was chromatographed on silica gel 60 (<230 mesh) eluting with ethyl acetate/petroleum ether 3:7. Starting material was eluted first and then the required compound as a pale yellow glass (5.23 g., 27%); $\nu_{max}$ (CHCl$_3$) 3400, 3000, 1770 and 1595 cm$^{-1}$; $\tau$ 2.3-2.8 (15H, m, phenyls), 3.75 (1H, broad s, lactam NH), 5.39 (2H, s, lactam C3 and C4), 6.82 (2H, s, S-CH$_2$) and 7.10 (1H, broad s, trityl NH).

EXAMPLE 3

1-(1-t-butoxycarbonyl-1-hydroxymethyl)-4-(3-iodopropargylthio)-3-triphenylmethylaminoazetidin-2-one

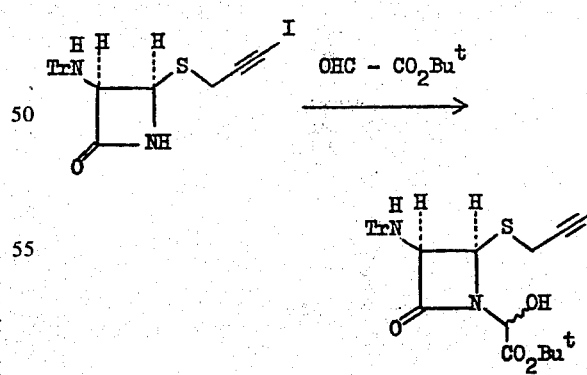

A solution of t-butyl glyoxalate (15.0 g.) in dry benzene (150 ml.) was heated at reflux in a Dean and Stark apparatus to remove any water. 4-(3-Iodopropargylthio)-3-triphenylmethylaminoazetidin-2-one (5.2 g.) was added and the solution heated at reflux under nitrogen for 4 hours. The cooled product was washed with water (8 × 40 ml.) and dried over sodium sulphate. The benzene was stripped off and the residue purified by chromatography on silica gel 60 (<230 mesh) (100 g.), eluting with ethyl acetate/petroleum ether (1:4) to yield a pale yellow foam (4.9 g., 76%); $\nu_{max}$ (CHCl$_3$) 3480, 2980, 1760, 1730 and 1595 cm$^{-1}$; τ (CDCl$_3$) 2.3–2.8 (15H, m, trityl),

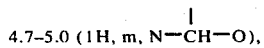
4.7–5.0 (1H, m, N—CH—O), 5.1–5.6 (2H,m, C3 and C4 β-lactam), 6.0 (1H, broad, OH or NH), 7.0 (1H, broad, OH or NH), 6.7–7.0 (2H,m, S-CH$_2$) and 8.50 (9H, s, t-butyl).

EXAMPLE 4

1-(1-t-Butoxycarbonyl-1-chloromethyl)-4-(3-iodopropargylthio)-3-triphenylmethylaminoazetidin-2-one

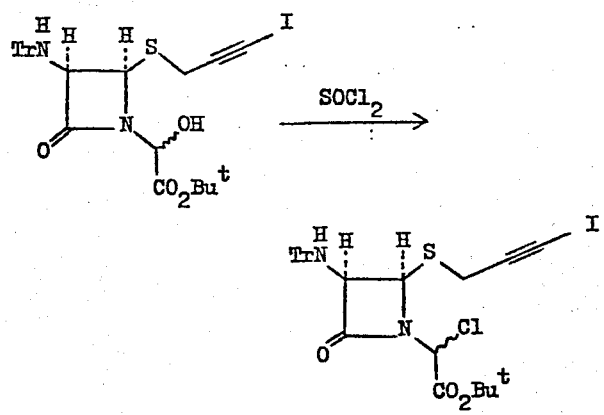

A solution of 1-(1-t-butoxycarbonyl-1-hydroxymethyl)-4-(3-iodopropargylthio)-3-triphenylmethylaminoazetidin-2-one (4.8 g.) in dry tetrahydrofuran (35 ml.) and dioxane (35 ml.) was cooled in an ice bath under nitrogen. It was treated with a solution of pyridine (1.8 ml.) in dioxane (3 ml.); and was followed by thionyl chloride (1.6 ml) in dioxane (3 mls). The mixture was stirred at ca. 10° for 30 minutes and then filtered. The filtrate was concentrated to dryness and extracted with anhydrous toluene (50 ml). The toluene solution was then evaporated to give a brown syrup (3.9 g., 79%); $\nu_{max}$ (CHCl$_3$) 2980, 1770, 1740 and 1600 cm$^{-1}$.

EXAMPLE 5

1-(1-t-Butoxycarbonyl-1-triphenylphosphoranylidenemethyl)-4-(3-iodopropargylthio)-3-triphenylmethylaminoazetidin-2-one

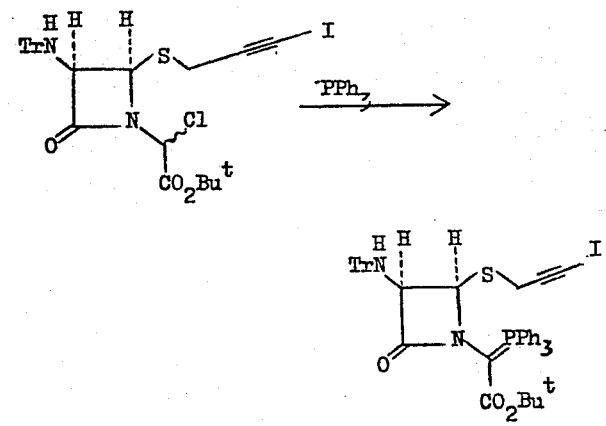

A solution of 1-(1-t-butyloxycarbonyl-1-chloromethyl)-4-(3-iodopropargylthio)-3-triphenylmethylaminoazetidin-2-one (3.9 g.) in dry dioxane (50 ml.) was treated with triphenylphosphine (4.5 g.) and 2,6-lutidine (0.8 ml.). The solution was heated at 50° under nitrogen for 12 hours. The product was concentrated under reduced pressure and the brown residue partitioned between ethyl acetate and brine. The organic phase was washed with brine, dried over sodium sulphate and concentrated. It was chromatographed on silica gel 60 (<230 mesh), eluting firstly with ethyl acetate/petroleum ether 1:4 to remove excess triphenylphosphine and then with ethyl acetate /60°–80° petroleum ether 1:1 to isolate the phosphorane as a pale yellow foam (3.0 g., 58%); $\nu_{max}$ (CHCl$_3$) 2960, 1745 and 1625 cm$^{-1}$; n.m.r. indistinct but following signals identified: τ (CDCl$_3$) 2.0–3.0 (m. phenyls), 5.02 (d J=4Hz, C4 β-lactam), 5.53 (dd J= 5&4Hz, C3 β-lactam) and 9.1 (s, t-butyl).

EXAMPLE 6

1-(1-Benzyloxycarbonyl-2-methyl-1-propenyl)-4-(3-phenylpropargylthio)-3-triphenylmethylaminoazetidin-2-one

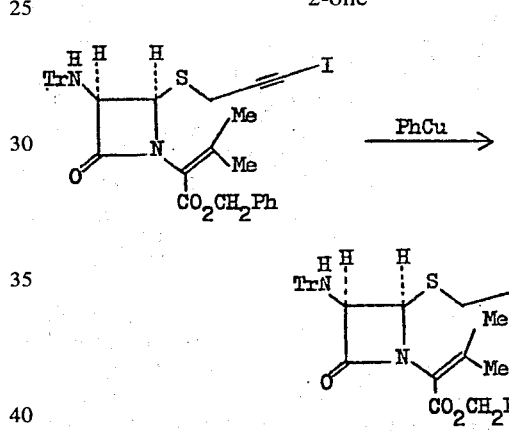

A suspension of cuprous bromide (92 mg.) in dry THF (5 ml.) was stirred and cooled in an ice bath and dry nitrogen was passed through the reaction vessel. A 1.8M. THF/benzene solution of phenyl lithium (0.36 ml.) was added to give a dark red-brown solution and after 5 mins., 1-(1-benzyloxycarbonyl-2-methyl-1-propenyl-4-(3-iodopropargylthio)-3-triphenylmethylaminoazetidin-2-one (350 mg.) in tetrahydrofuran (3 ml.) was added. The reaction mixture was stirred and allowed to warm to room temperature. After 2 hrs. the product was concentrated under reduced pressure, dissolved in benzene (10 ml.) and centrifuged to remove the solids. The benzene supernatent solution was concentrated and applied to a column of silica gel 60 (<230 mesh). The required product was obtained by eluting with ethyl acetate/60°–80° petroleum ether 1:4. It was a white crystalline solid (180 mg., 56%); m.p. 139°–141°; $\nu_{max}$ (CHCl$_3$) 3000, 1760, 1720, 1625 and 1595 cm$^{-1}$; τ (CDCl$_3$) 2.3–2.9 (25H,m, phenyl), 5.03 (2H, s, benzyl CH$_2$), 5.07 (1H, d J=5Hz, C4 β-lactam), 5.45 (1H, dd, J=8&5Hz, C3 β-lactam), 7.01 (1H, d J=8Hz, NH), 6.87 and 7.21 (2H, ABq J=17Hz, S-CH$_2$), 7.84 (3H, s, ⇀CH$_3$) and 8.00 (3H, s,⇀CH$_3$).

EXAMPLE 7

1-(1-t-Butoxycarbonyl-1-triphenylphosphoranylidenemethyl)-4-(3-phenylpropargylthio)-3-triphenylmethylaminoazetidin-2-one

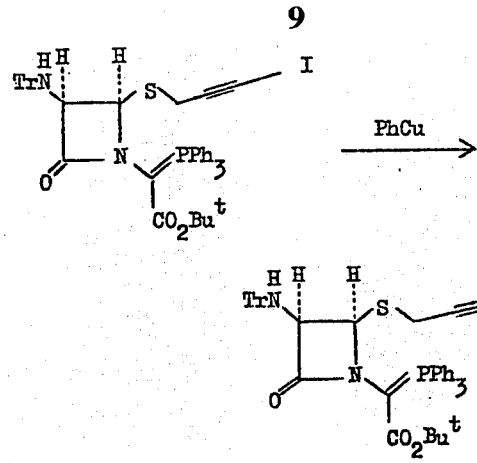

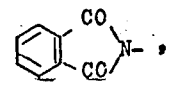

A suspension of cuprous bromide (105 mg.) in dry THF (8 ml.) was stirred in an ice bath under nitrogen. It was treated with a 1.8M. THF/benzene solution of phenyl lithium (0.41 ml.) to give a red-brown solution. After 5 mins. a solution of 1(1-t-butoxycarbonyl-1-triphenylphosphoranylidenemethyl)-4-(3-iodopropargylthio)-3-triphenylmethylaminoazetidin-2-one (500 mg.) in dry tetrahydrofuran (5 ml.) was added. The reaction mixture was stirred at room temperature for 3 hours and then the solvent was stripped off under reduced pressure. The residue was extracted with benzene (10 ml.), centrifuged to remove the solids. The liquid was concentrated and purified by column chromatography on silica gel 60 (<230 mesh) eluting with ethyl acetate/60°–80° petroleum ether 1:2. The product was a pale yellow foam (253 mg., 53%); $\nu_{max}$ (CHCl$_3$) 2980, 1745 and 1630 cm$^{-1}$; $\nu_{max}$(EtOH) 225 nm and 250 nm (shoulder).

The product was further characterised by using the method of J. H. C. Nayler, M. J. Pearson and R. Southgate (J.C.S. Chem. Comm. 1973, 58) to convert it to 3-benzyl-4-t-butoxycarbonyl-7-triphenylmethylaminoceph-3-em; m.p. 159°–160°.

What we claim is:

1. A compound of the formula (I):

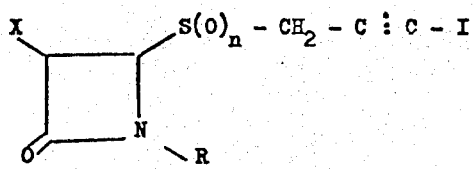

(I)

wherein $n$ is 0 or 1, X is selected from the group consisting of Ph$_3$C.NH,

(CH$_3$)$_3$C.O.CO.NH-, Cl$_3$C.CH$_2$.O.CO.NH-, Ph.CH$_2$.CO.NH- and Ph.O.CH$_2$.CO.NH- and R is hydrogen or a group of the formula (II) or (III):

$$\begin{matrix} R_2 \\ R_1 \end{matrix} \quad (II) \qquad \begin{matrix} R_3 \\ R_1 \end{matrix} \quad (III)$$

wherein R$_1$ is benzyloxycarbonyl, t-butoxycarbonyl, 2,2,2-trichloroethoxycarbonyl, diphenylmethoxycarbonyl, p-methoxybenzyloxycarbonyl, p-nitrobenzyloxycarbonyl or p-methoxyphenoxycarbonyl, R$_2$ is OH or Cl and R$_3$ is C(CH$_3$)$_2$ or PR$_a$R$_b$R$_c$ wherein R$_a$, R$_b$ and R$_c$ are each alkyl of 1 to 6 carbon atoms phenyl, toluyl or benzyl.

2. A compound of the formula (VII):

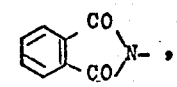

(VII)

wherein X is selected from the group consisting of Ph$_3$C.NH,

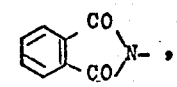

(CH$_3$)$_3$C.O.CO.NH-, Cl$_3$C.CH$_2$.O.CO.NH-, Ph.CH$_{and}$ $_{Ph.O.CH2}$.CO.NH-. .CO.NH-.

3. 4-(3-Iodopropargylthio)-3-triphenylmethylaminoazetidin-2-one.

4. A compound according to claim 1 wherein R$_a$, R$_b$ and R$_c$ are each phenyl.

5. A compound according to claim 2 wherein X is triphenylmethylamino, phenylacetamido or phenoxyacetamido.

* * * * *

UNITED STATES PATENT AND TRADEMARK OFFICE
CERTIFICATE OF CORRECTION

PATENT NO. : 3,951,951

DATED : April 20, 1976

INVENTOR(S) : TERENCE CHARLES SMALE

It is certified that error appears in the above—identified patent and that said Letters Patent are hereby corrected as shown below:

Claim 2, last two lines should read:

-- $(CH_3)_3C.O.CO.NH-$, $Cl_3C.CH_2.O.CO.NH-$, $Ph.CH_2CO.NH-$ and $Ph.O.CH_2.CO.NH-$. --

Signed and Sealed this

Sixth Day of July 1976

[SEAL]

Attest:

RUTH C. MASON
*Attesting Officer*

C. MARSHALL DANN
*Commissioner of Patents and Trademarks*